United States Patent
Shipp et al.

(10) Patent No.: US 6,958,069 B2
(45) Date of Patent: Oct. 25, 2005

(54) INSTRUMENTS AND METHODS FOR USE IN LAPAROSCOPIC SURGERY

(75) Inventors: John I. Shipp, Tullahoma, TN (US); Jeffrey P. White, Milford, CT (US)

(73) Assignee: Mark LoGuidice, Southport, CT (US)

( * ) Notice: Subject to any disclaimer, the term of this patent is extended or adjusted under 35 U.S.C. 154(b) by 30 days.

(21) Appl. No.: 10/047,122

(22) Filed: Jan. 15, 2002

(65) Prior Publication Data

US 2002/0137988 A1 Sep. 26, 2002

Related U.S. Application Data

(60) Provisional application No. 60/261,798, filed on Jan. 17, 2001.

(51) Int. Cl.$^7$ .............................................. A61B 17/22
(52) U.S. Cl. ...................................... 606/127; 606/207
(58) Field of Search ................................. 606/113, 114, 606/115, 127, 128, 205, 206, 207; 604/167.02, 167.04, 164.1, 164.03

(56) References Cited

U.S. PATENT DOCUMENTS

| | | | |
|---|---|---|---|
| 4,347,846 A | 9/1982 | Dormia | |
| 4,611,594 A | 9/1986 | Grayhack et al. | |
| 4,807,626 A | 2/1989 | McGirr | |
| 5,037,379 A | 8/1991 | Clayman et al. | 600/37 |
| 5,074,867 A | 12/1991 | Wilk | 606/128 |
| 5,143,082 A | 9/1992 | Kindberg et al. | 600/37 |
| 5,147,371 A | 9/1992 | Washington et al. | 606/127 |
| 5,176,687 A | 1/1993 | Hasson et al. | 606/114 |
| 5,190,554 A | 3/1993 | Coddington, III et al. | 606/113 |
| 5,190,561 A | 3/1993 | Graber | 606/127 |
| 5,192,284 A | 3/1993 | Pleatman | 606/114 |
| 5,281,230 A | 1/1994 | Heidmueller | 606/127 |
| 5,312,417 A | 5/1994 | Wilk | 606/114 |
| 5,320,627 A | 6/1994 | Sorensen et al. | 606/167 |
| 5,341,815 A | 8/1994 | Cofone et al. | 600/37 |
| 5,351,680 A | 10/1994 | Jung | |
| 5,370,647 A | 12/1994 | Graber et al. | 606/127 |
| 5,431,676 A | 7/1995 | Dubrul et al. | 606/185 |
| 5,465,731 A | 11/1995 | Bell et al. | 600/37 |
| 5,480,404 A | 1/1996 | Kammerer et al. | 606/113 |
| 5,486,183 A | 1/1996 | Middleman et al. | 606/127 |
| 5,527,274 A | * 6/1996 | Zakko | 604/28 |
| 5,630,805 A | 5/1997 | Ternamian | 604/274 |
| 5,643,227 A | * 7/1997 | Stevens | 604/264 |
| 5,643,282 A | 7/1997 | Kieturakis | 606/114 |
| 5,643,313 A | 7/1997 | Levin | 606/198 |
| 5,647,372 A | 7/1997 | Tovey et al. | 600/37 |
| 5,681,324 A | 10/1997 | Kammerer et al. | 606/113 |
| 5,814,058 A | 9/1998 | Carlson et al. | 606/185 |
| 5,827,319 A | 10/1998 | Carlson et al. | 606/191 |
| 5,836,913 A | 11/1998 | Orth et al. | 604/107 |
| 5,843,017 A | 12/1998 | Yoon | 604/22 |
| 5,853,399 A | 12/1998 | Sasaki | 606/167 |
| 5,893,878 A | * 4/1999 | Pierce | 606/207 |
| 5,906,622 A | 5/1999 | Lippitt et al. | 606/127 |

(Continued)

FOREIGN PATENT DOCUMENTS

GB       3301       of 1879

Primary Examiner—Cary E. O'Connor
(74) Attorney, Agent, or Firm—Martin & Ferraro, LLP

(57) ABSTRACT

A surgical dilator extractor is introduced into the abdominal cavity through a trocar cannula and expanded, forming a tissue receiving space, at the distal end. The tissue that is to be extracted is then manipulated into the space with a grasper inserted through a lumen in the dilator extractor. The tissue is then removed from the cavity by the surgeon applying a force onto the dilator extractor that insures the elongation of the tissue and temporarily dilates the entry wound to the extent necessary for the tissue to be removed. Alternative embodiments of the surgical dilator extractor and related instrument tool sets and methods for the use thereof also are disclosed.

84 Claims, 10 Drawing Sheets

U.S. PATENT DOCUMENTS

| | | | |
|---|---|---|---|
| 5,908,435 A | 6/1999 | Samuels | 606/200 |
| 5,924,175 A | 7/1999 | Lippitt et al. | 24/537 |
| 5,944,728 A | 8/1999 | Bates | 606/127 |
| 5,971,995 A | 10/1999 | Rousseau | 606/114 |
| 6,036,708 A | 3/2000 | Sciver | 606/159 |
| 6,080,174 A | 6/2000 | Dubrul et al. | 606/185 |
| 6,099,550 A * | 8/2000 | Yoon | 606/205 |
| 6,162,235 A | 12/2000 | Vaitekunas | 606/169 |
| 6,280,450 B1 * | 8/2001 | McGuckin, Jr. | 606/114 |
| 6,350,267 B1 | 2/2002 | Stefanchik | 606/114 |
| 6,383,195 B1 | 5/2002 | Richard | 606/114 |
| 2002/0068943 A1 * | 6/2002 | Chu et al. | 606/114 |

* cited by examiner

INSTRUMENTS AND METHODS FOR USE IN LAPAROSCOPIC SURGERY

RELATED APPLICATIONS

This application claims the benefit of U.S. Provisional Application No. 60/261,798, filed Jan. 17, 2001, incorporated by reference herein.

BACKGROUND

The present invention relates generally to mechanical devices and methods used in laparoscopic surgical procedures to remove organs and excised tissue from internal body cavities.

It will be appreciated by those skilled in the art that the use of bags or pouches to remove organs and large tissue specimen during laparoscopic surgical procedures is well known. As described, for example, in U.S. Pat. No. 5,147,371 a pouch is introduced into the abdominal cavity for retrieving gallstones and tissue. The bag is opened and closed using a wire loop as a drawstring. In U.S. Pat. No. 5,192,284 an expandable bag is inserted into the abdominal cavity through a trocar cannula. The bag described in the '284 patent is made of a memory material that is rigid enough to support itself. The bag expands and remains open when it is inserted into the abdominal cavity through the cannula. U.S. Pat. No. 5,480,404 describes a pouch for extracting tissue that is opened and closed by a ratchet mechanism. U.S. Pat. No. 5,341,815 employs shape memory effect metal to open the bag upon insertion through a trocar. U.S. Pat. Nos. 5,681,324 and 5,971,995 describe similar bags and pouches.

The pouches described in these patents are useful in containing any bile or gallstones that might otherwise spill into the abdominal cavity during extraction of a torn gallbladder. These type of devices, however, suffer from at least two problems. Since such devices are closed on the distal end, air inside the enclosure tends to balloon the pouches or bags during the extraction process thereby increasing the size or not allowing a full collapse of a bag as it is removed from the wound. Additionally, when the tissue is larger than the wound size it is forced to the bottom of the bag as the radial force of the wound acts on the tissue during extraction. This also increases the size to which the wound must be dilated for removal of the tissue. Tapering the bags toward the distal end helps somewhat to lessen this effect, but the result is not optimal and does not fully address the problem of air trapped in the bag.

Since the goal of laparoscopic surgery is to become less invasive by using smaller entry wounds the prior art is of limited value for removing large specimens through, for example 5 mm wounds. When the user pulls on the bag in an attempt to remove it through a small trocar entry wound the specimen is forced to the bottom of the bag by the radial forces exerted by the abdominal tissue or by the forces exerted on the bag from the cannula thus creating a large lump that is often incapable of passing through the wound. The use of this type of extraction bag in these cases often requires de-bulking of the specimen so that the bagged specimen pieces are of such a size that the bag can be extracted through the trocar entry wound, typically 10–12 mm. This is a time consuming process that is not always successful since, for example, large stones may be inside a gallbladder and it also compromises the pathologic examination of the tissue specimen. Alternately the wound size is increased with a scalpel to allow the extraction, thereby lessoning the advantage of the laparoscopic surgery. Additionally, these types of extraction bags add undue complexity to the procedure since they require the use of two ports, one for the bag and the second for a grasper to retrieve the tissue and put it into the bag.

U.S. Pat. Nos. 5,190,561 and 5,370,647 to Graber disclose several embodiments of laparoscopic extraction devices that allow a grasper to be inserted into the center of an extractor device so that tissue can be more easily manipulated into the inside of the extractor. In each of the embodiments the extractor is introduced into the abdominal cavity through a specially designed trocar cannula equipped with setscrews to lock the extractor to the trocar cannula. Upon exiting the distal end of the cannula, the distal end of the extractor expands, much like an umbrella. A grasper is then introduced into the abdominal cavity through a lumen in the extractor. The specimen is grasped and pulled into the expanded open distal end of the extractor, a cone shaped device. The grasper is then locked to the cannula using the setscrews. The proximal end of the extractor is equipped with a handle, which is used to pull the extractor and the tissue through the cannula. As the handle is pulled upward " . . . the enveloping means collapses around the tissue and returns to its pre-deployment." Thus the enveloping means of Graber '647 is relied on to compress the tissue to a size that allows it to be drawn into the shroud 610, as shown in FIG. 13. Thus, the device is not optimally designed to deal with a tissue specimen that will not compress to a point so that it can be drawn through the shroud.

The extractor of Graber '647 also has several other disadvantages. The Graber '647 device cannot be used with standard trocars since it utilizes setscrews, not generally available on trocars in current use, to lock it to the trocar, and it utilizes an expensive locking mechanism to lock the grasper to the extractor. In addition, most abdominal laparoscopic procedures are performed with the abdominal cavity insufflated with carbon dioxide. The lumen in the extractor of Graber '647 has no provision for sealing and thus when the extractor is placed through the trocar cannula's seal, the abdomen would loose its carbon dioxide pressure. The Graber '647 device is removed from the body cavity by an exertion force on the handle of the device. This unduly places rotational and shear forces on the extractor-grasper lever lock and the extractor-trocar setscrews in the case of a trocar cannula that employ screw threads to insure anchorage in the abdominal wall, since these cannula require rather vigorous rotational manipulation to remove them from the abdominal wall.

The extractor cover disclosed in the Graber '647 patent is made from "a sturdy waterproof, stain resistant fabric such as treated sailcloth or duck cloth." These materials are thick and bulky and therefore, are not useful for extractors for less invasive trocar cannula such as 5 mm and smaller devices, since multi-folds of the cover is required for the extractor to pass through small-bore cannula. FIG. 24 of the '647 patent discloses a thin "baggie," however, it requires thick leaves 608 and a plunger rod 606 to compress the tissue. The thickness of these unduly complicating features makes the Graber device ill-suited for small cannulas.

The embodiment disclosed in FIG. 12 of the '647 patent teaches the use of a flexible, waterproof web material with an opening mouth so that tissue can enter the rib portion 510. While this embodiment partially solves the spillage problem it unduly complicates manipulating the tissue inside the extractor and is overly complex in that the extractor cover and the spillage compartment are made of two separate pieces and must be joined by sewing, heat treating, or welding.

Laparoscopic removal of the gallbladder has, heretofore, entailed the use of four entry cannula, typically two of which are 10/12 mm in diameter and two of which are 5 mm in diameter. The two 5 mm ports are used to accept instruments such as scissors, graspers, electro-surgery probes, and suction/irrigation devices. The 10/12 mm ports are employed to allow the use of 10 mm endoscopes attached to a camera for viewing the surgical field, to allow a clip applier for ligating vessels and ducts, and to allow the removing of the gallbladder following its excision.

In an effort to make the procedure less invasive, 5 mm clip appliers have been developed, such as the one described by Shipp et al. in U.S. Pat. No. 5,858,018. The 5 mm clip applier allows the conversion of one of the two 10/12 mm ports to a third 5 mm port. The remaining 10/12 mm port prior to this invention has been required to accept 10 mm endoscopes and to allow for the removal of the gallbladder, usually through the umbilicus port site. New bright 5 mm endoscopes coupled with more sensitive cameras have been developed that are quite acceptable substitutes for the prior art camera systems. These new developments leave the gallbladder removal through a 5 mm or smaller port as the last obstacle to the full conversion of the process to four much less invasive 5 mm ports. The conversion from two 10 mm and two 5 mm trocars to all 5 mm trocars lowers the entry wounds area by 50 percent, which greatly reduces bleeding and post surgery incisional herniation at the wound sites.

What is needed then is a simple, inexpensive device and a simple, easy to use method for rapid removal of tissue, such as a gallbladder, from a wound site that is smaller than the specimen and one that does not require a substantial secondary operation such as grinding the specimen into smaller pieces, or require that the wound be significantly enlarged.

SUMMARY OF THE INVENTION

The present invention in one embodiment is directed to an expandable dilator extractor that expands upon entry into the abdominal cavity for acceptance of a tissue specimen using a grasper to pull the specimen into the interior of the dilator extractor. The construction of the dilator is such that when a surgeon places an upward force, away from the surface of the abdomen on the deployed dilator, it first causes features inside the tissue space of the dilator extractor to minimize the cross section of the tissue, and thus minimize the wound dilation requirement. This in turn decreases the force required to remove the tissue. The features inside the tissue space of the dilator extractor also preferably grip the tissue so as to keep the tissue in the elongated state and to prevent its motion downward towards the abdominal cavity as the radial forces of the trocar puncture wound act upon it during extraction. Finally, the resulting elongated conical shape forces the trocar puncture wound to expand to allow the larger specimen to be extracted with a minimum of tearing or otherwise permanently enlarging the wound.

The present invention also is directed to a method and describes an apparatus for easily removing fluid from tissue, such as bile from a gallbladder, to further reduce the tissue size prior to extraction.

In another embodiment, the tissue may be treated to partially dissolve the tissue and thus reduce the extraction force. To reduce yet even further the extraction force, the current invention in another preferred embodiment utilizes a very thin, low friction material in contact with the wound.

In another preferred embodiment, the distal end of the cover is open so that no ballooning occurs. Alternatively, the distal end of the cover is drawn up in a drawstring purse fashion. The pursed section is drawn somewhat proximally so that the bottom formed by the purse will serve to retain gallstones and small amounts of bile yet still allows the escape of entrapped gas, thus avoiding ballooning.

In another preferred embodiment the cover is allowed to vent by virtue of being constructed of breathable material such as GoreTeX™, or by virtue of appropriately placed venting holes. The dilator extractor of the present invention preferably employs a seal in the form of a valve at the proximal end to insure against loss of peritoneal pressure when a grasper or other tool is inserted or removed through its cannula into the abdominal cavity.

DESCRIPTION OF THE PREFERRED EMBODIMENTS

Reference will now be made in detail to the present preferred embodiments (exemplary embodiments) of the invention, examples of which are illustrated in the accompanying drawings. Wherever possible, the same reference numbers will be used throughout the drawings to refer to the same or like parts.

Figure 1:
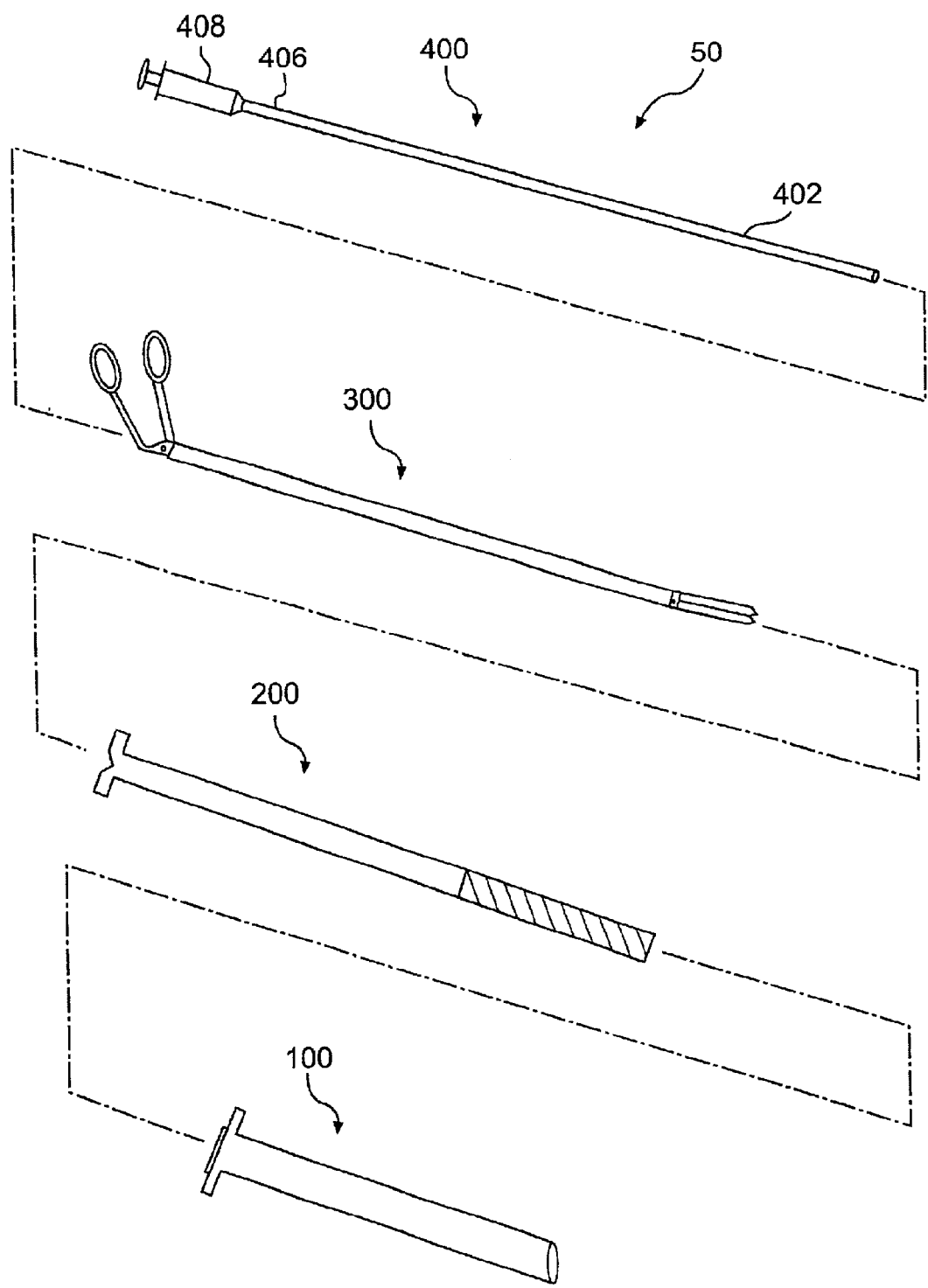
FIG. 1 is a diagrammatic view of a syringe with a needle, a grasper, a dilator extractor, and a cannula in accordance with one embodiment of the present invention.
Figure 9:
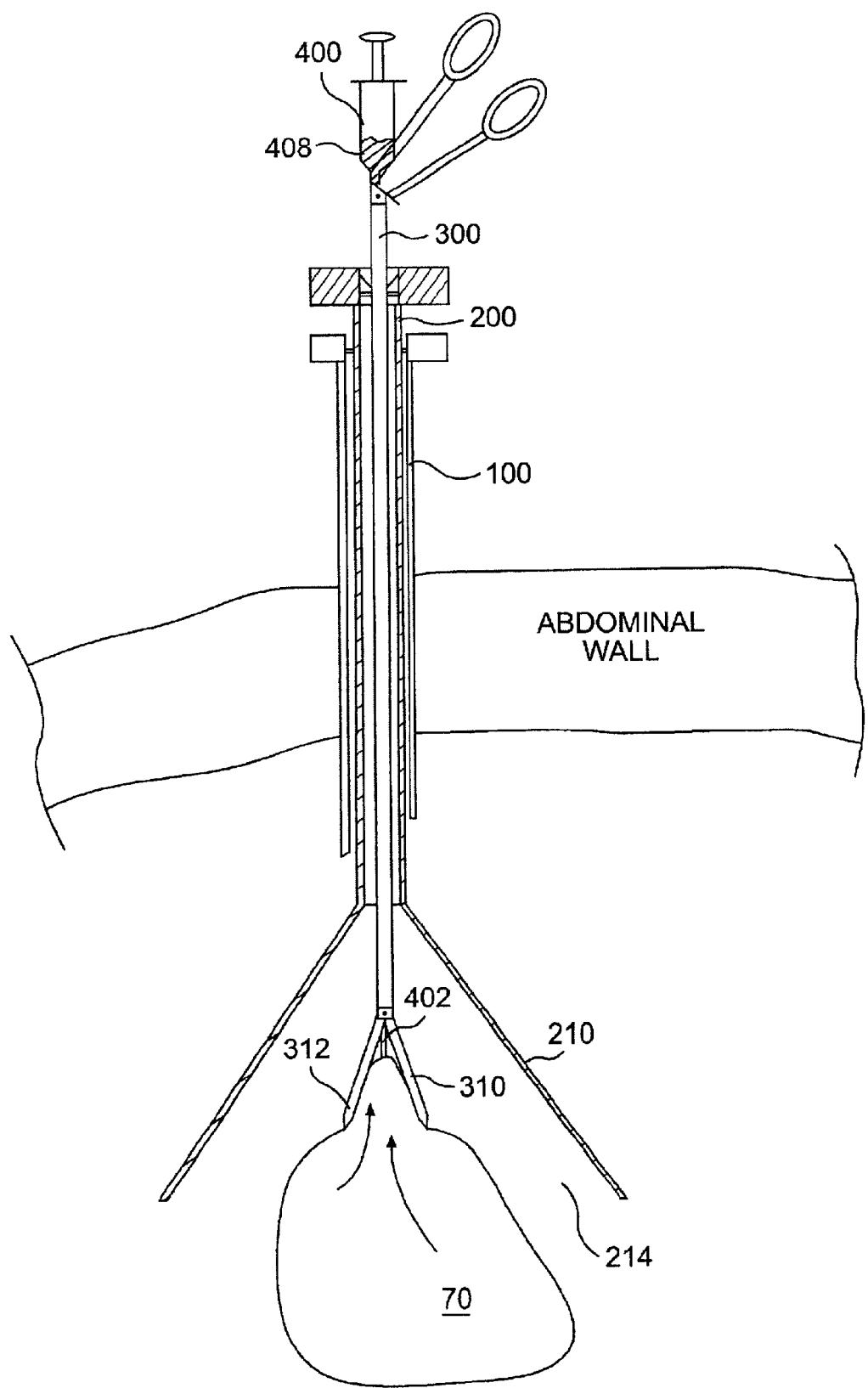
FIG. 9 is a side elevation view of a syringe, grasper, dilator extractor, and cannula inserted in the abdominal wall of a patient, the grasper being inserted in the dilator extractor, the dilator extractor being inserted in the cannula, the dilator extractor and cannula being shown in cross section with a tissue specimen being aspirated in accordance with the instrumentation and method of the present invention.

FIG. 1 shows a tool set 50 having a cannula 100, a dilator extractor 200, a grasper 300, and syringe device 400. As shown in FIGS. 1 and 9, syringe 400 is insertable in grasper 300, which is in turn insertable in dilator extractor 200, which in turn is insertable in cannula 100 to form a multi-coaxial assembly for use in laparoscopic surgery.

Referring to FIGS. 2–4 and 8, dilator extractor 200 is inserted into a pressurized abdominal cavity 60 through the abdominal wall of a patient. Dilator extractor 200 enters through valve 102 at trailing end 106 of cannula 100.

Dilator extractor 200 includes a body 202 having a leading end 204, a trailing end 206, a longitudinal axis L, and a lumen 208. Body 202 includes a dilator 210 at leading end 204 that is movable between an unexpanded position, shown in FIG. 2, and an expanded position, shown in FIG. 8. Trailing end 206 preferably includes a depth-limiting protrusion in the form of shoulder 207. Shoulder 207 is adapted to limit the depth of insertion of dilator extractor 200 into cavity 60 of the patient.

When the trailing end portion of dilator 210 clears leading end 104 of cannula 100, dilator 210 expands to the expanded position owing to memory elements 212, thus forming a truncated conical-shaped tissue receiving space 214, enclosed by a dilator cover 216.

Figure 2:
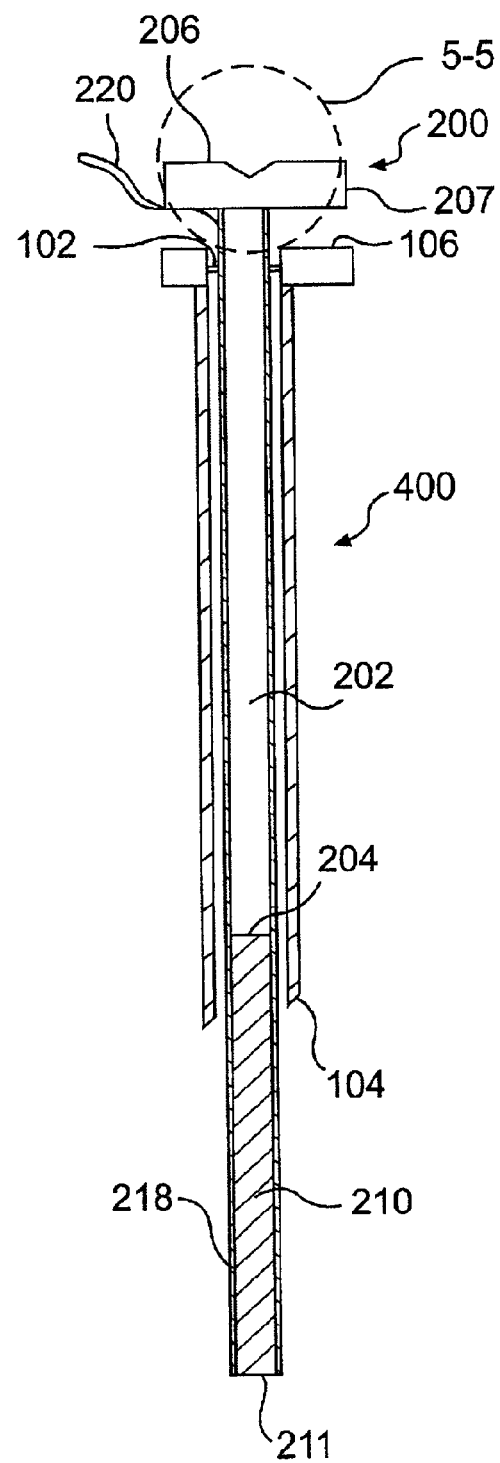
FIG. 2 is a partial side sectional view of the dilator extractor of FIG. 1 inserted in the cannula of FIG. 1.

FIG. 2 shows dilator extractor 200 before dilator 210 clears leading end 104 of cannula 100. Dilator 210 may be preserved in the unexpanded position because of the restraints of a later described retainer 218 or the inner diameter of cannula 100. In the unexpanded position memory elements 212 are elastically bent inward to permit dilator 210 to have a maximum lateral dimension preferably in the range of 3 mm to 5 mm. Dilator cover 216 is preferably wrapped around memory elements 212 to allow the passage of dilator extractor 200 in the unexpanded position through cannula 100.

In a preferred embodiment, retainer 218 maintains dilator extractor 200 in the unexpanded state. One suitable retainer is straw-shaped and encircles dilator 210. Retainer 218 extends toward trailing end 206 of dilator extractor 200 terminating into a graspable surface grip 220 proximate trailing end 206. The composition of retainer 218 is such that it is strong enough to restrain the spring forces of dilator 210, yet an upward force on graspable surface grip 220 will cause retainer 218 to peel open allowing dilator 210 to expand. By way of example, a suitable strength welded seam in a polyurethane film can accomplish such a peeling feature.

Figure 3:
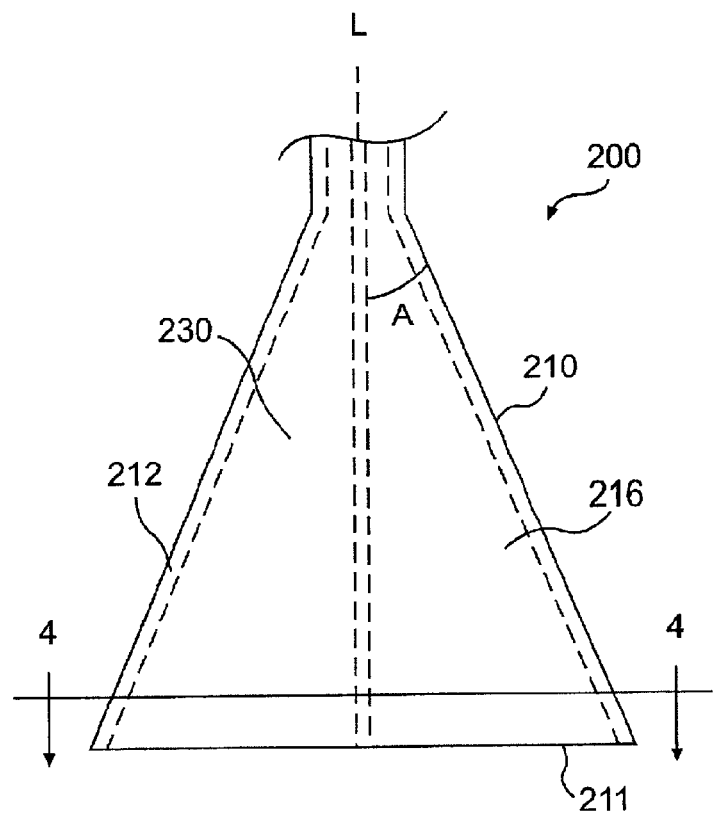
FIG. 3 is a partial side elevation view of the leading end of the dilator extractor of FIG. 1 in an expanded position.
Figure 4:
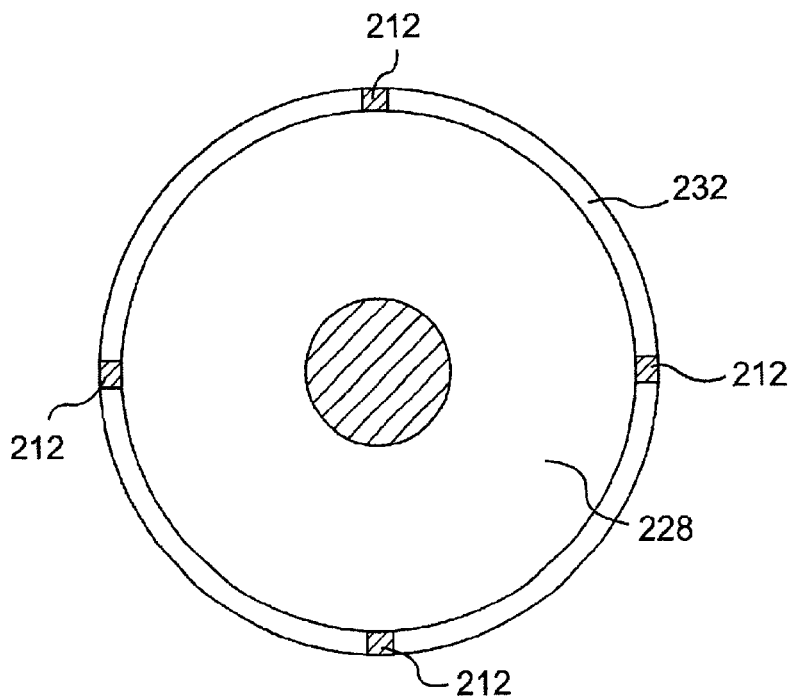
FIG. 4 is a bottom plan view along line 4—4 of FIG. 3.

FIGS. 3 and 4 show dilator 210 in the expanded position. In a preferred embodiment, flat steel wire is formed to an appropriate expansion angle to form memory elements 212. Preferably, four such wires are attached to body 202 of dilator extractor 200 using appropriate fasteners or by welding them to body 202. In alternate embodiments, memory elements 212 may include alternate memory materials such as certain types of polymers and may be integral extensions of dilator extractor 200. Stamped and rolled stainless steel also would provide a dilator such that the memory elements are integral to the body of the device.

Memory elements 212 are preferably parallel to the longitudinal axis of dilator extractor 200 when dilator extractor is in the unexpanded position. As shown in FIG. 3, when dilator extractor 200 is in the expanded position, memory elements 212 preferably expand dilator 210 to form an angle A between cover 216 of dilator 210 and the longitudinal axis of dilator extractor 200 of at least 10 degrees, more preferably 20 degrees.

Although four longitudinal memory elements 212 are preferred, other forms of memory elements are sufficient for the purpose of expanding dilator 210. For example, a single memory element may be positioned at leading end 211 of dilator 210 and adapted to run along the circumference of leading end 211. Other circumferential memory elements may be concentrically included between leading end 211 and leading end 204 of body 202 along dilator 210. As a further example, a single memory element may form a conical coil adapted to expand dilator 210 in both a longitudinal and axially transverse direction.

Figure 8:
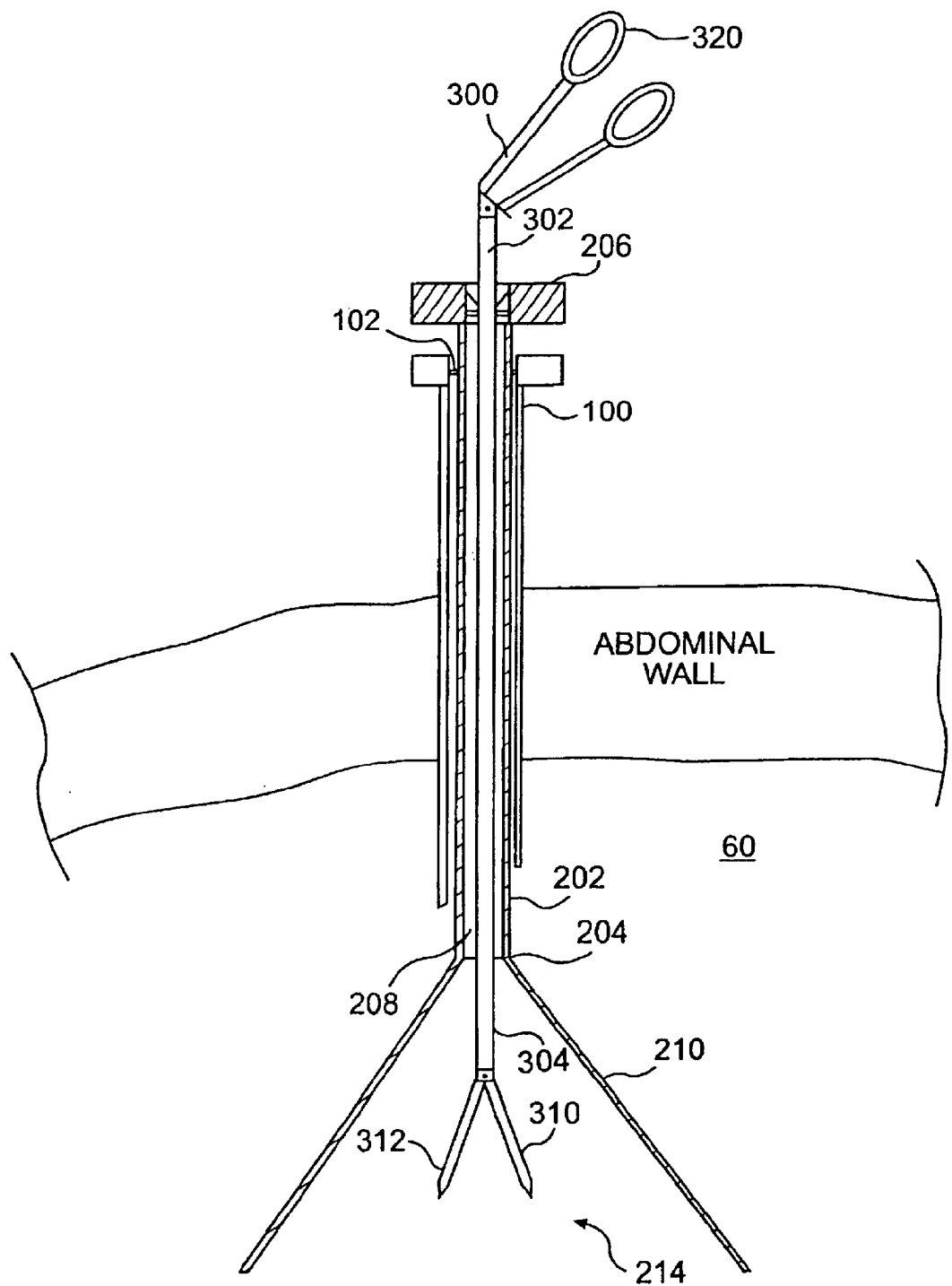
FIG. 8 is a side elevation view of a grasper, dilator extractor, and cannula inserted in the abdominal wall of a patient, the grasper being inserted in the dilator extractor, the dilator extractor being inserted in the cannula, the dilator extractor and cannula being shown in cross section with the dilator extractor in the expanded position.

Once dilator 210 of dilator extractor 200 is in the expanded position as depicted in FIG. 8, grasper 300, in a preferred embodiment, is inserted through channel or lumen 208, into tissue space 214, and into cavity 60.

Figure 5:
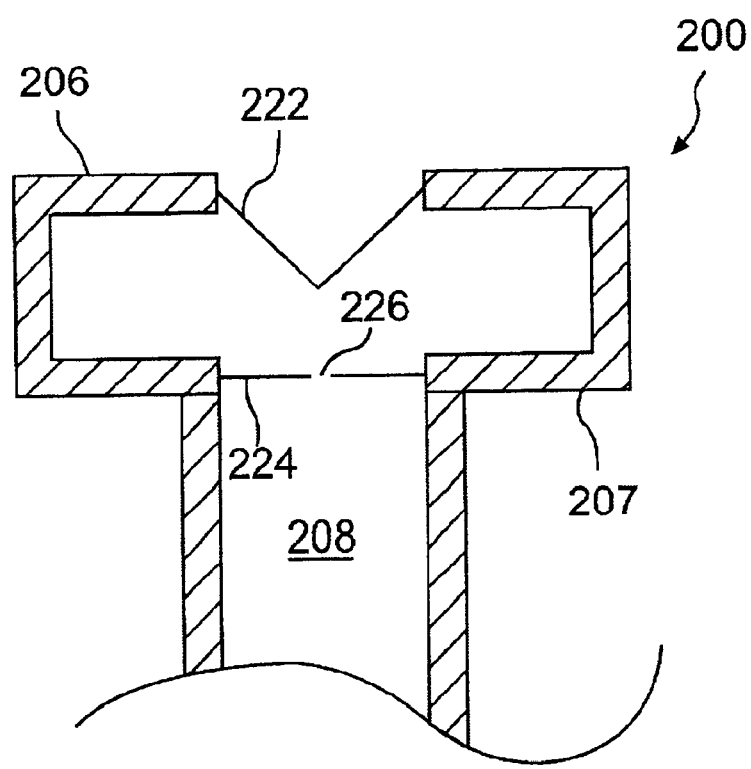
FIG. 5 is an enlarged fragmentary cross sectional view along line 5—5 of FIG. 2.

As shown in FIG. 5, trailing end 206 preferably includes first and second seals 222, 224, respectively. First seal 222 preferably forms a duckbill "V" shaped valve made of a resilient material that forms a seal when no instrument is inserted into lumen 208. Second seal 224 is preferably formed of a resilient material containing a through hole 226 in its center. Through hole 226 is preferably smaller than the maximum cross sectional dimension of the instrument that the through hole is adapted to receive and forms a seal when the instrument is inserted into lumen 208. For example, both seals may preferably be configured to permit the passage of grasper 300 therethrough while inhibiting a loss of pressure from within the patient. It is appreciated that more than or less than two seals may be used without departing from the scope of the present invention.

As shown in FIG. 9, excised tissue 70 is grasped by jaws 310, 312 of grasper 300 and pulled inside conical tissue space 214. First and second seals 222, 224 seal around the outside diameter of grasper 300 so that pressure inside cavity 60 is maintained as grasper 300 and tissue 70 are manipulated. Once tissue 70 is inside conical tissue space 214, the entire assembly (grasper 300, dilator extractor 200, trocar cannula 100, and tissue 70) is ready for extraction.

Figure 10:
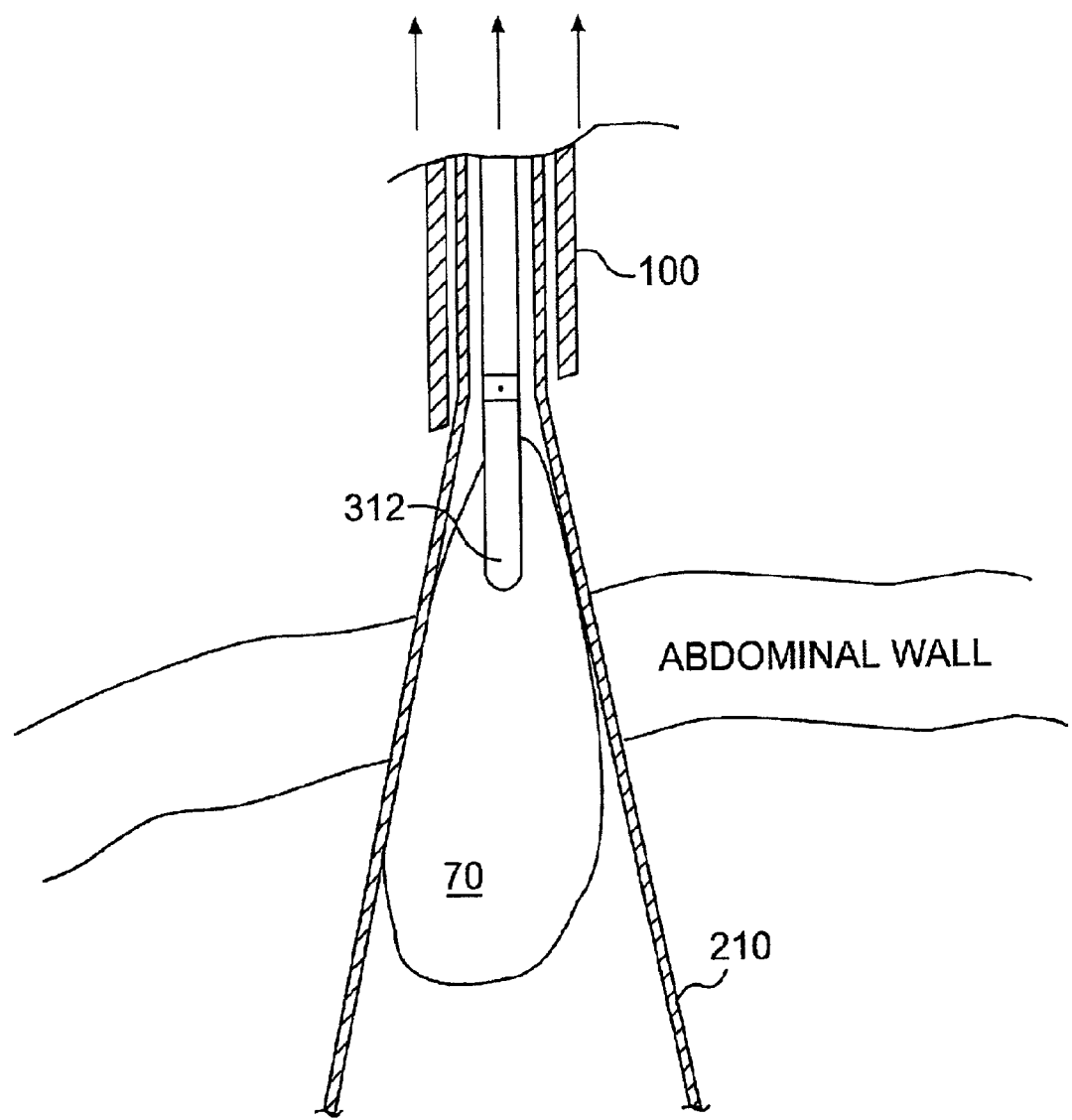
FIG. 10 is a partial side elevation view of the grasper, dilator extractor, and cannula of FIG. 9 being withdrawn from the abdominal cavity with the tissue specimen in accordance with the instrumentation and method of the present invention.

In instances where the tissue specimen is larger than the inside diameter of cannula 100, such as would usually be the case for a gallbladder specimen with a 5 mm cannula for example, dilator 210 will close somewhat under the influence of the upward force of the surgeon until memory elements 212 and the tissue resilient forces offset the radial forces asserted by the abdominal wall. At this point conical tissue space 214 of dilator extractor 200 will no longer contract and grasper 300, dilator extractor 200, and cannula 100 will be locked together in a more or less rigid fashion. This condition is depicted in FIG. 10. Dilator extractor 200 is constructed in such a manner that application of additional force causes the wedge shape of dilator 210 to begin to increase or dilate the trocar wound in the abdominal wall as the surgeon applies more and more upward force. The larger the specimen, the larger the force necessary to dilate the abdominal wall wound to a size large enough to allow the entire assembly to be removed. The tensile strength of dilator 210 must be adequate to withstand the extraction force. The shape of the trocar puncture wound is important to insure against tearing of the entry wound. A slit entry wound rather than star-shaped entry wound is preferred.

Figure 6:
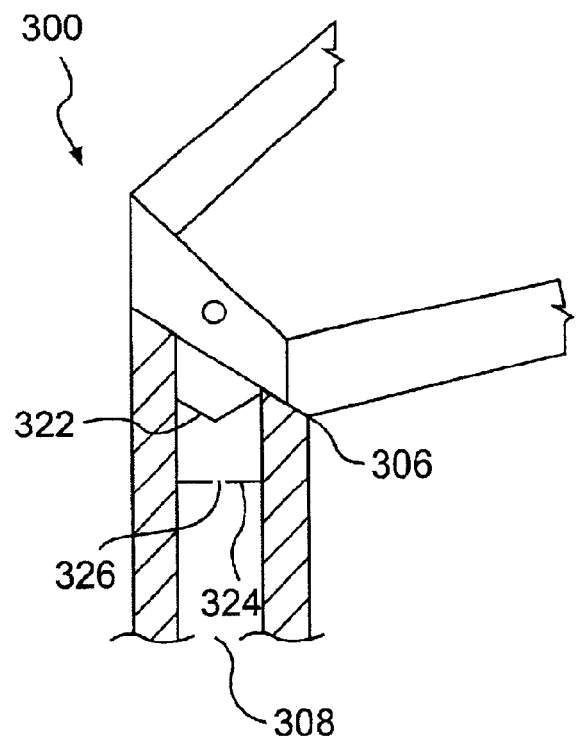
FIG. 6 is a partial side sectional view of the trailing end of a shaft of the grasper of FIG. 1 with a valve and a seal.
Figure 7:
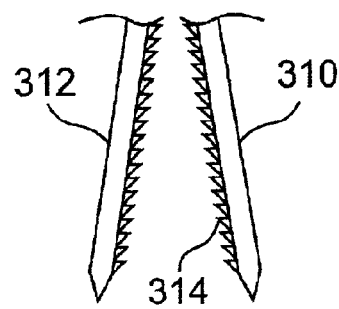
FIG. 7 is a partial side elevation view of a pair of jaws at the leading end of a grasper.

Grasper 300, as shown in FIGS. 1 and 6–8, has a shaft 302 having a leading end 304, a trailing end 306, and a lumen 308 through the center of shaft 302 that can be occupied by a hollow needle 402 of syringe device 400. Shaft 302 includes jaws 310, 312 at leading end 304 for grasping tissue therebetween. As shown in FIG. 7, jaws 310, 312 preferably include surface roughenings such as ridges 314 on the grasping surface of each jaw. As will be appreciated by those of skill in the art, grasper 300 may be adapted to have more than two jaws. For example, a third jaw maybe used to provide a third grasping surface for grasping the tissue. It will be further appreciated that other jaw configurations are possible and within the scope of the present invention. Jaws 310, 312 may have a smooth grasping surface, or may have ridges 314.

Shaft 302 preferably has a length in the range of 15 cm to 35 cm and an outside maximum cross sectional dimension of less than 5 mm. Lumen 308 of shaft 302 preferably has an inside maximum cross sectional dimension in the range of 1 mm to 4 mm.

As shown in FIGS. 6 and 8, trailing end 306 of grasper 300 includes a pair of handles 320 for moving jaws 310, 312 relative to one another. Trailing end 306 also preferably includes first and second seals 322, 324, respectively. First seal 322 preferably forms a duckbill "V" shaped valve made of a resilient material that forms a seal when no instrument is inserted into lumen 308. Second seal 324 is preferably formed of a resilient material containing a through hole 326 in its center. Through hole 326 is preferably smaller than the maximum cross sectional dimension of the instrument that the through hole is adapted to receive and forms a seal when the instrument is inserted into lumen 308. For example, both seals may preferably be configured to permit the passage of needle 402 therethrough while inhibiting a loss of pressure from within the patient. It is appreciated that more than or less than two seals may be used without departing from the scope of the present invention.

Trailing end 306 preferably includes a depth-limiting protrusion for limiting the depth of insertion of grasper 300 into the cavity. The depth-limiting protrusion may be formed as a shoulder, or may form a part of handles 320.

As shown in FIGS. 1 and 9, trailing end 406 of needle 402 extends beyond grasper handles 320, and is fitted with a hypodermic syringe 408. Needle 402 is movable distally so that it punctures the grasped tissue, for example, a gallbladder. Gallbladders that are distended with bile can thus be drained before extraction by aspirating the bile up through needle 402 and into syringe 408. Alternately, suction for removing the bile can be supplied from any vacuum source such as an aspirator.

This embodiment allows for grasping, tissue manipulation, removal of bile, and extraction all through a single port site. Significantly, one embodiment of needle 402 and grasper 300 allows for the tissue to be firmly grasped by grasper 300 yet needle 402 can still pass through leading end 304 of grasper 300 into the tissue such as a gallbladder where it performs evacuation of the bile.

In one preferred embodiment cover 216, as best shown in FIGS. 3 and 4, is preferably made of a laminated, flexible, material that will allow it to be folded and contained in cannula 100 prior to expansion of dilator 210 of dilator extractor 200. Cover 216 includes an inner surface 228 and an outer surface 230.

Outer surface 230 of cover 216 preferably is made of a material having a low coefficient of friction, such as a low porosity PTFE (polytetrafluoroethylene). Inner surface 228 is preferably made of a material having a high coefficient of friction, such as coarse weave polyester or nylon. It will be appreciated by those skilled in the art that other materials are suitable for providing a coefficient of friction that is higher on inner surface 228 than outer surface 230 and are within the scope of the present invention. Preferably, the coefficient of friction of inner surface 228 is in the range of 0.5 to 1.0. The two materials are preferably laminated together to form a cell migration barrier 232 to avoid viable cancer cells that might be contained in the excised tissue from coming into contact with the trocar site wound. The low friction outer surface 230 of cover 216 minimizes the force required for extraction while the high friction inner surface 228 provides a gripping force on the tissue surface area and thereby minimizes the force transferred to the grasper/tissue interface during the dilation extraction process. The dilation forces acting on the dilator require that the tensile strength of cover 216 is adequate to withstand the friction force exerted by the tissue on inner surface 228. Bifurcated PTFE and coarse woven polyester with a total thickness of the lamination of approximately 0.005 inches exhibits a tensile strength of about 10,000 PSI. This will accommodate a friction force between the tissue and cover 216 of about 30 pounds without the material of the cover tearing. The upward force placed on the apparatus by the surgeon is divided between cover 216 and the grasper-tissue interface, thus without significant friction between the inside of cover 216 and the tissue, all the extraction force is transmitted to the grasper-tissue interface.

Figure 11:
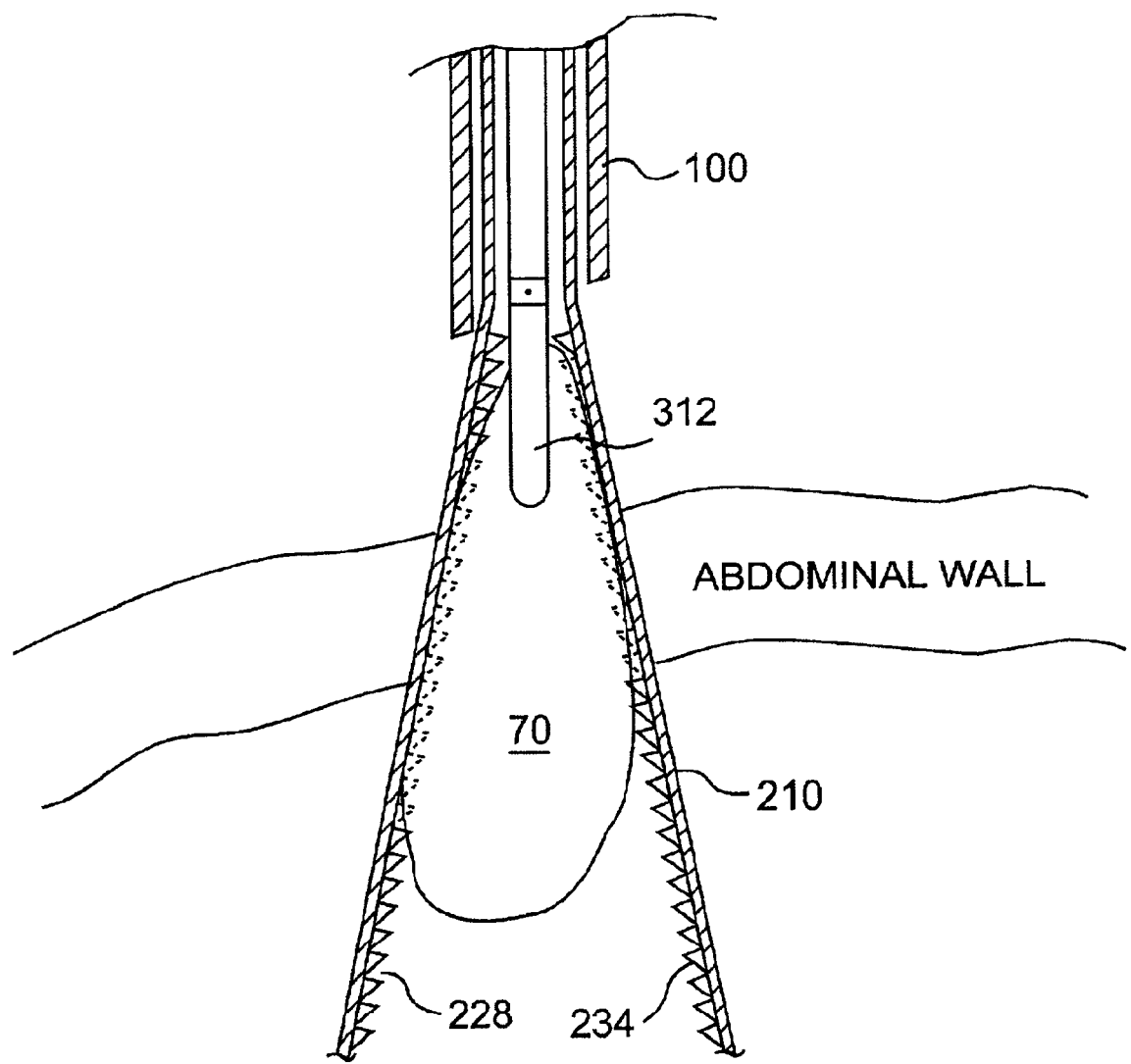
FIG. 11 is a side elevation view of a grasper and cannula with another embodiment of a dilator extractor of the present invention having tissue engaging protrusions being withdrawn from the abdominal cavity with the tissue specimen.

FIG. 11 shows an alternate embodiment inner surface 228 of cover 216. Memory elements 212 are equipped with tissue retaining protrusions such as teeth 234. Preferably, teeth 234 are generally pointed toward trailing end 206 when dilator 210 is in the expanded position so that as dilator 210 closes around the tissue as shown in FIG. 11, teeth 234 bite into the tissue, thus supplying the dominance of the counter acting force to the extraction force rather than the friction of the tissue against inner surface 228 of cover 216.

It will be appreciated by those skilled in the art that other forms of tissue retaining protrusions are suitable for gripping the tissue, for example, tabs, ridges, and knurling. Additionally, the tissue retaining protrusions are preferably uniformly spaced around the longitudinal axis of dilator extractor 200 to provide an even distribution of retaining force against the tissue. Tissue retaining protrusions may also be spaced substantially about the entire area of inner surface 228 of cover 216. Tissue retaining protrusions may be formed on cover 216, memory elements 212, or a combination thereof. Forming tissue retaining protrusions on memory elements 212 provides additional stability when withdrawing the assembly from the wound site. Preferably, the tissue retaining protrusions are adapted to grab the tissue without penetrating it in order to reduce the risk of content spillage from the tissue.

Figure 12:
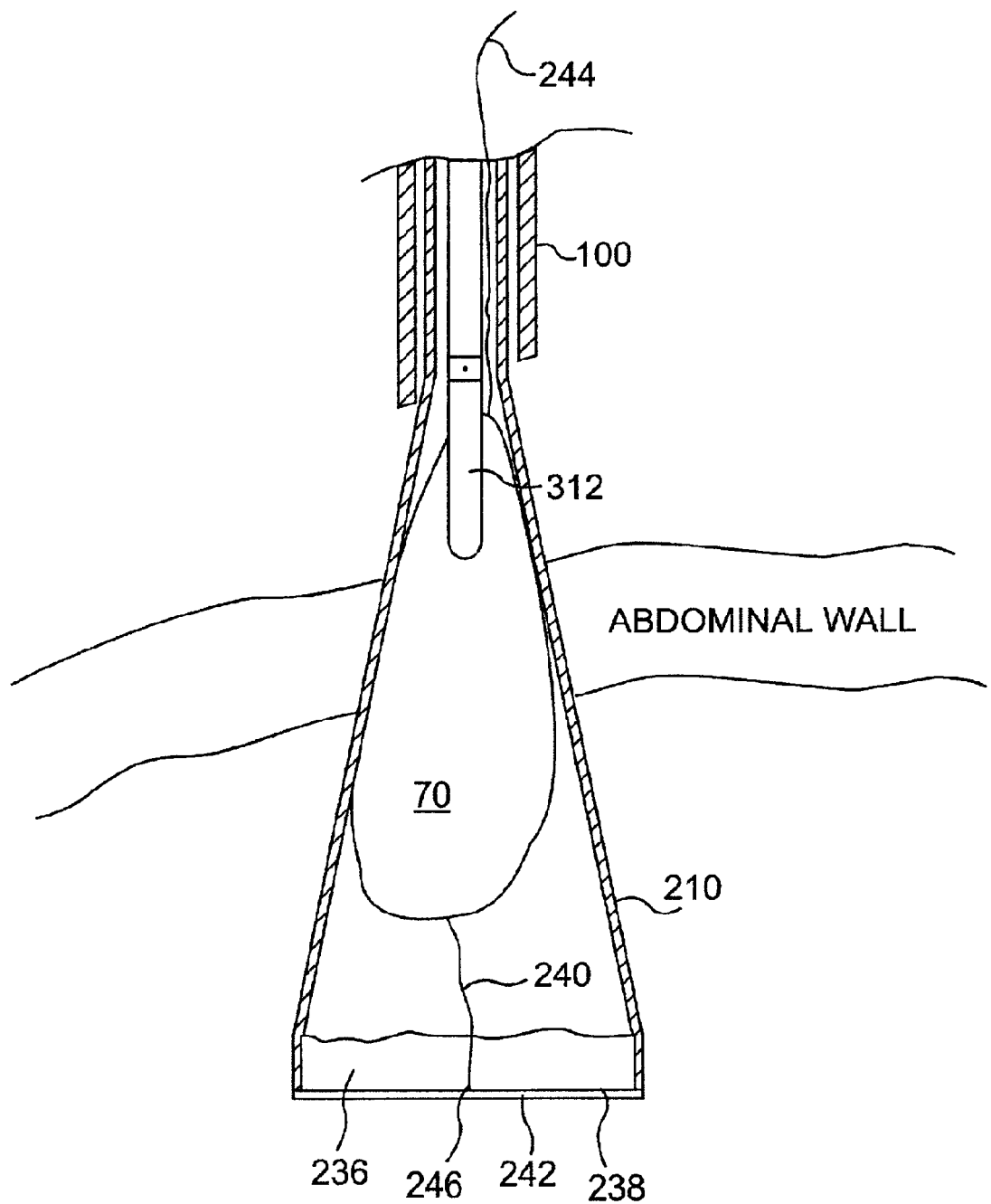
FIG. 12 is a side partial cross sectional elevation view of a grasper and cannula with another embodiment of a dilator extractor of the present invention having a draw cable prior to being drawn in and withdrawn from the abdominal cavity with the tissue specimen.

FIG. 12 shows another alternate embodiment of the present invention. Dilator 210 preferably includes an elongated cover portion 236 beyond the distal end of memory elements 212. Elongated cover portion 236 preferably has a hem 238 that at least partially encloses a draw cable 240 at its leading end 242. Draw cable 240 has a proximal end 244 adapted to lie beyond trailing end 306 of dilator extractor 200 and a distal end 246 adapted to close leading end 242 of elongated cover portion 236. Distal end 246 of draw cable 240 is fed proximally through dilator extractor lumen 208 and out through seals 222, 224. Preferably, distal end 246 of cable 240 is adapted to circumscribe the perimeter of cover 216 to form at least one loop around the longitudinal axis of dilator extractor 200, preferably at hem 238. More than one loop may be formed to provide greater strength for drawing in leading end 211 of dilator 210.

In using draw cable 240, the tissue is manipulated into tissue space 214. The surgeon then pulls draw cable 240 proximally, thus drawing in leading end 242 of elongated cover portion 236 like a drawstring purse. The pursed section is drawn somewhat proximally so that the bottom formed by the purse will serve to retain tissue and contents therein such as gallstones and small amounts of bile, yet still allow the escape of entrapped gas, thus avoiding ballooning.

Cover 216 of dilator 210 may be breathable or vented to avoid ballooning. Alternatively, vents with valves may be incorporated in the side of body 202 to vent off gases as the tissue is being extracted.

Having described the apparatus, methods for its use will now be described. It should be understood that the order disclosed is only preferred and that the steps may be performed in other orders while still being within the scope of the present invention. Additionally, some steps may be repeated as necessary.

A preferred method of removing tissue from the abdominal cavity is shown in FIGS. 8–10. Cannula 100 is inserted through the abdominal wall and into cavity 60, which is preferably pressurized. Preferably a cannula having a maximum diameter in the range of 3 mm to 5 mm is used in order to make the procedure less invasive. Dilator extractor 200 is inserted into cannula 100 through seal 102 to a position where leading end 211 of dilator 210 extends beyond leading end 104 of cannula 100. Dilator 210 is expanded to form tissue extraction space 214. Grasper 300 is inserted into dilator extractor 200 through seals 222, 224 and through lumen 208. The tissue is grasped by grasper 300 and manipulated into tissue space 214. If desired, grasper 300 may be locked to dilator extractor 200 to provide more stability. If dilator extractor 210 includes elongated cover portion 236, the surgeon may pull draw cord 240 at proximal end 244 to draw in elongated cover portion 236, thus substantially trapping the tissue and any of its contents in tissue receiving space 214. Next, an upward force is exerted on dilator extractor 200, dilating the trocar wound such that the tissue is removed from the cavity under the influence of the upward force.

Alternately, for tissue containing a fluid such as bile in a gallbladder, additional steps may be included such as suctioning out the fluid prior to the extraction step. For example, needle 402 of syringe device 400 is inserted into grasper 300 through seals 322, 324 and through lumen 308 to a position where leading end 404 of needle 402 extends beyond leading end 204 of body 202 of dilator extractor 200. Fluid is then suctioned from the tissue through needle 402 by syringe 408. It will be appreciated that vacuum sources other than syringe 408 may be used to aspirate the tissue, for example, an aspirator. It will be further appreciated that aspiration may occur during other phases of the operation prior to the extraction of the tissue from the wound site. For example, needle 402 may be inserted through lumen 208 of dilator extractor 200 and fluid suctioned from the tissue before grasper 300 is inserted or used.

To further reduce the extraction force needed to withdraw the assembly with the tissue, the tissue may be treated to at least partially dissolve the tissue or its contents, for example, gallstones of a gallbladder. A syringe may be used to inject a composition capable of dissolving tissue. One example of such a composition is methyl tert-butyl ether. The tissue is treated preferably after fluid is suctioned. It will be appreciated that the tissue may be treated irrespective of any fluid suction.

Simulated dilator extractors were built and tested in the abdominal cavity of a swine. Aluminum cones of varying base diameters representing varying tissue sizes simulated the dilator section. Abdominal access for the cones was gained through a 100 mm incision along the midline of the animal. A 5 mm trocar with a single sided cutting tip obturator (rather than the more common three side pyramidal tip) was used to entry the cavity through a circular 5 mm wound located approximately 30 mm to the left of the midline. Each of four simulators consisting of 5 mm cylinders, 100 mm long transitioning into truncated cones with 5 mm diameter tops tapering to bases of 15, 20, 25, 30 mm diameters respectively, were separately tested by inserting them through the access incision. The 5 mm trocar was then inserted into the abdominal cavity, the obturator removed, and the 5 mm simulator tops were then inserted from the distal of the cannula so that they were exposed above the cannula valve. A force gage was then attached to the exposed section. The vertical pull force required to dilate the 5 mm puncture wound so that the cone was total extracted from the animal was then measured with a calibrated force gage. A new 5 mm trocar site was used for each of the four cones. The extraction force is shown in the table below:

| Cone Base Diameter, mm | Upward Extraction Force, lbs |
| --- | --- |
| 15 | 12 |
| 20 | 21 |
| 25 | 37 |
| 30 | 50 |

Each measurement was repeated using the same puncture wound to test the extent to which the wound had been torn or permanently stretched. The data indicated that dilation of 2 to 3 times is possible. Up to 20–25 mm the forces are of reasonable magnitude to make the device practical. The minimizing wound size is important to minimizing postoperative hernias and other complications.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for aspirating material from an animal or human body cavity, the method comprising the steps of:
   inserting an instrument adapted to manipulate the tissue through the body cavity, the instrument having a passage therein;
   suctioning fluid from the tissue through the passage of the instrument; and
   dilating the cavity to remove tissue that is unable to fit completely within a cannula without substantial compression of the tissue.

2. The method of claim 1, further comprising the step of grasping the tissue with the instrument to remove the tissue from the cavity.

3. The method of claim 1, further comprising the step of treating the tissue to at least partially dissolve the tissue or any contents in the tissue.

4. The method of claim 3, wherein the treating step includes the sub-step of treating the tissue with methyl tert-butyl ether.

5. The method of claim 3, wherein the treating step is performed through the passage of the instrument.

6. The method of claim 1, further comprising the steps of inserting a cannula into the cavity, the cannula having a lumen adapted to accept the instrument.

7. The method of claim 1, wherein the dilating step is performed by the instrument.

8. The method of claim 7, wherein the instrument is a surgical extractor having a dilator.

9. The method of claim 1, wherein the suctioning step includes the step of suctioning bile from a gall bladder.

10. The method of claim 1, wherein the inserting step includes the step of inserting a cannula having a maximum diameter in the range of 3 mm to 5 mm.

11. The method of claim 1, further comprising the step of removing the tissue from the cavity.

12. A method for removing tissue from an animal or human body cavity that is unable to fit completely within a cannula without substantial compression, the method comprising the steps of:
    inserting the cannula into the cavity;
    inserting a dilator having a leading end through the cannula;
    expanding the leading end of the dilator to an expanded position;
    inserting a grasper through the dilator;
    grasping the tissue with the grasper;
    moving the tissue with the grasper into the dilator; and
    removing the cannula and the dilator together with the dilator remaining substantially in the expanded position.

13. The method of claim 12, further comprising step of retaining the tissue within the expanded leading end of the dilator.

14. The method of claim 12, wherein the step of removing includes removing the dilator having a generally conical shape in the expanded position.

15. The method of claim 12, further comprising the step of suctioning fluid or other material from the tissue.

16. The method of claim 15, wherein the suctioning step includes the step of suctioning bile or other material from a gall bladder.

17. The method of claim 12, wherein the leading end of the dilator includes a draw cable for drawing in the leading end of the dilator, further comprising the step of pulling the draw cable to draw in the leading end of the dilator.

18. The method of claim 12, wherein the step of inserting the cannula includes inserting a cannula having a maximum diameter in the range of 3 mm to 5 mm.

19. A surgical tool set for removing tissue from an animal or human body cavity, said tool set comprising:
    a surgical extractor dilator having a leading end, a trailing end, a length therebetween, and a lumen between the leading and trailing ends, said leading end having a dilator movable between an unexpanded position and an expanded position;
    a grasper insertable within said lumen of said surgical extractor dilator, said grasper having a leading end with grasping surfaces, a trailing end with a handle, and a lumen between the leading and trailing ends, said lumen of said grasper adapted to permit the passage of a surgical instrument therethrough, said grasper having a length greater than the length of said surgical extractor dilator; and
    an elongated needle adapted to insert within said lumen of said grasper, said needle having a length sufficient to extend beyond a distal end of said grasper.

20. The surgical tool set of claim 19, wherein said needle is adapted to be connected to a syringe.

21. The surgical tool set of claim 19, wherein said needle is adapted to be connected to an aspirator.

22. The surgical tool set of claim 19, further comprising a cannula for providing protected access to a surgical site, said cannula having a leading end, a trailing end, a length therebetween, and a lumen between the leading and trailing ends adapted to permit passage of said surgical extractor dilator therethrough.

23. The surgical tool set of claim 22, wherein said cannula has a maximum outer diameter less than 10 mm.

24. The surgical tool set of claim 23, wherein said cannula has a maximum outer diameter in the range of 3 mm to 5 mm.

25. The surgical tool set of claim 19, further comprising at least one seal oriented within said lumen of said surgical extractor dilator configured to permit the passage of said grasper therethrough while inhibiting a loss of pressure from within the body cavity after said surgical extractor dilator is inserted in the patient.

26. The surgical tool set of claim 25, wherein said at least one seal has a through-hole smaller than the maximum cross sectional dimension of said grasper.

27. A surgical extractor for moving tissue from an animal or human body cavity, the extractor comprising:
    a body having a leading end, a trailing end, a longitudinal axis, and a lumen between said leading and trailing ends;
    a dilator at the leading end of said body being movable between an unexpanded position and an expanded position, said dilator having an inner surface; and
    tissue retaining protrusions on said inner surface of said dilator, said tissue retaining protrusions being uniformly spaced around the longitudinal axis of said body and being configured to generally point towards said trailing end of said body when said dilator is in the expanded position.

28. The surgical extractor of claim 27, wherein said tissue retaining protrusions are teeth.

29. The surgical extractor of claim 27, wherein said tissue retaining protrusions are spaced substantially about the entire area of said inner surface.

30. The surgical extractor of claim 27, wherein said dilator includes a memory element configured to expand said dilator from the unexpanded position to the expanded position.

31. The surgical a extractor of claim 30, wherein said dilator includes memory elements parallel to the longitudinal axis when said dilator is in the unexpanded position.

32. The surgical extractor of claim 30, wherein said memory element is adapted to expand said leading end of said dilator to an angle of at least 10 degrees from the longitudinal axis of said surgical extractor.

33. The surgical extractor of claim 30, wherein said memory element is adapted to expand said leading end of said dilator to an angle of at least 20 degrees from the longitudinal axis of said body.

34. The surgical extractor of claim 27, further comprising a retainer around at least a portion of said dilator for maintaining said dilator in the unexpanded position, said retainer being adapted to be removed from said dilator, thereby allowing said dilator to move to the expanded position.

35. The surgical extractor of claim 27, wherein said dilator has a maximum diameter in the range of 3 mm to 5 mm in the unexpanded position.

36. The surgical extractor of claim 27, wherein said tissue retaining protrusions are formed from a memory element.

37. A surgical extractor for removing tissue from an animal or human body cavity, the extractor comprising: a body having a leading end, a trailing end, a longitudinal axis, and a lumen between said leading and trailing ends;

a dilator at the leading end of said body being movable between an unexpanded position and an expanded position, said dilator having an inner surface, said dilator including a cell migration barrier formed between at least two different materials; and tissue retaining protrusions on said inner surface of said dilator, said tissue retaining protrusions being uniformly spaced around the longitudinal axis of said body.

38. The surgical extractor of claim 37, wherein one of said materials is PTFE.

39. The surgical extractor of claim 37, wherein one of said materials is polyester.

40. The surgical extractor of claim 37, wherein said tissue retaining protrusions are teeth.

41. The surgical extractor of claim 37, wherein said tissue retaining protrusions are spaced substantially about the entire area of said inner surface.

42. The surgical extractor of claim 37, wherein said dilator includes a memory element configured to expand said dilator from the unexpanded position to the expanded position.

43. The surgical extractor of claim 42, wherein said dilator includes memory elements parallel to the longitudinal axis when said dilator is in the unexpanded position.

44. The surgical extractor of claim 42, wherein said memory element is adapted to expand said leading end of said dilator to an angle of at least 10 degrees from the longitudinal axis of said surgical extractor.

45. The surgical extractor of claim 42, wherein said memory element is adapted to expand said leading end of said dilator to an angle of at least 20 degrees from longitudinal axis of said body.

46. The surgical extractor of claim 37, further comprising a retainer around at least a portion of said dilator for maintaining said dilator in the unexpanded position, said retainer being adapted to be removed from said dilator, thereby allowing said dilator to the expanded position.

47. The surgical extractor of claim 37, wherein said dilator has a maximum diameter in the range of 3 mm 5 mm in the unexpanded position.

48. The surgical extractor of claim 37, wherein said tissue retaining protrusions are formed from a memory element.

49. A surgical extractor for removing tissue from an animal or human body cavity, the extractor comprising:

a body having a leading end, a trailing end, a longitudinal axis, and a lumen between said leading and trailing ends;

a dilator at the leading end of said body being movable between an unexpanded position and an expanded position said dilator having an inner surface and a memory element configured to expand said dilator from the unexpanded position to a expanded position, said memory element being along a circumference of said dilator; and tissue retaining protrusions on said inner surface of said dilator, said tissue retaining protrusions being uniformly spaced around the longitudinal axis of said body.

50. The surgical extractor of claim 49, wherein said memory element is positioned at a leading end of said dilator.

51. The surgical extractor of claim 49, wherein said tissue retaining protrusions are teeth.

52. The surgical extractor of claim 49, wherein said tissue retaining protrusions are spaced substantially about the entire area of said inner surface.

53. The surgical extractor of claim 49, wherein said memory element is adapted to expand and said leading end of said dilator to an angle of at least 10 degrees from the longitudinal axis of said surgical extractor.

54. The surgical extractor of claim 49, wherein said memory element is adapted to expand said leading end said dilator to an angle of at least 20 degrees from the longitudinal axis of said body.

55. The surgical extractor of claim 49, further comprising a retainer around at least a portion of said dilator for maintaining said dilator in the unexpanded position, a said retainer being adapted to be removed from said dilator, thereby allowing said dilator to move to the expanded position.

56. The surgical extractor of claim 49, wherein said dilator has a maximum diameter in the range of 3 mm to 5 mm in the unexpanded position.

57. The surgical extractor of claim 49, wherein said tissue retaining protrusions are formed from a memory element.

58. A surgical extractor for removing tissue from an animal or human body cavity, the extractor comprising:

a body having a leading end, a trailing end, a longitudinal axis, and a lumen between said leading and trailing ends; and a dilator at the leading end of said body being movable between an unexpanded position and an expanded position, said dilator having an inner surface made substantially of a first material and an outer surface made substantially of a second material, said first material of said inner surface having a coefficient of friction greater than a coefficient of friction of said second material of said outer surface.

59. The surgical extractor of claim 58, wherein the coefficient of friction of said inner surface of said dilator is in a range from 0.5 to 0.9.

60. The surgical extractor of claim 58, wherein said dilator includes a cell migration barrier formed between at said first and second materials.

61. The surgical extractor of claim 58, wherein one of said materials is PTFE.

62. The surgical extractor of claim 58, wherein one of said materials is polyester.

63. The surgical extractor of claim 58, further comprising surface roughenings along said inner surface.

64. The surgical extractor of claim 58, further comprising protrusions adapted to grab tissue without penetrating the tissue.

65. A surgical extractor for removing tissue from an animal or human body cavity, the extractor comprising:

a body having a leading end, a trailing end, a longitudinal axis, and a lumen between said leading and trailing ends;

a dilator at the leading end of said body being movable between an unexpanded position and an expanded position; and a retainer for restricting said dilator in the unexpanded position, said retainer being adapted to be removed from said dilator, thereby allowing said dilator to move to the expanded position, said retainer including a grip proximate said trailing end of said body for peeling open said retainer.

66. The surgical extractor of claim 65, wherein said retainer comprises a polyurethane film.

67. A surgical extractor for removing tissue from an animal or human body cavity of a patient, the extractor comprising:
- a body having a leading end, a trailing end, a longitudinal axis, and a lumen between said leading and trailing ends;
- a dilator at the leading end of said body being movable between an unexpanded position and an expanded position, said dilator having a leading end;
- a cover at the leading end of said dilator adapted to capture the tissue prior to the extraction thereof from the patient; and
- a draw cable running through said lumen of said body, and having at least one loop at the leading end of said cover, said draw cable being adapted to draw in said cover upon moving said draw cable away from the trailing end of said body.

68. The surgical extractor of claim 67, wherein said cover includes a hem enclosing at least a portion of said draw cable.

69. The surgical extractor of claim 67, wherein said draw cable is adapted to run from said cover through said lumen of said body and lie beyond said trailing end of said body.

70. The surgical extractor of claim 67, wherein said cover has a perimeter and a distal end of said draw cable is adapted to circumscribe the perimeter of said cover to form said a least one loop.

71. The surgical extractor of claim 70, wherein said draw cable is adapted to form a plurality of loops around the perimeter of said cover.

72. The surgical extractor of claim 67, wherein said cover is made from a breathable material.

73. The surgical extractor of claim 67, wherein said cover is watertight.

74. A method for removing tissue from an animal or human body cavity, the method comprising the steps of:
- inserting a cannula into the cavity;
- inserting a dilator into the cannula, the dilator having a leading end with a cover attached thereto, the cover having draw cable adapted to draw in the cover;
- expanding the leading end of the dilator to an expended position;
- moving the tissue into the dilator; and
- drawing the draw cable.

75. The method of claim 74, wherein the drawing step includes the step of drawing the draw cable to draw in the cover while the tissue is within the cavity.

76. The method of claim 74, further comprising the step of dilating the cavity to remove the tissue.

77. The method of claim 74, further comprising the steps of inserting a grasper through the cannula and grasping the tissue with the grasper to remove the tissue from the cavity.

78. The method of claim 74, wherein the draw cable has a distal end attached to the cover an a proximal end lying outside the cannula, the pulling step including the sub-step of pulling the proximal end of the draw cable to draw in the cover.

79. A method of removing tissue from an animal or human body cavity, the method comprising the steps of:
- inserting a cannula into the body cavity;
- inserting a dilator having a leading end through the cannula;
- expanding the leading end of the dilator to an expanded position;
- inserting a grasper having a passage into the body cavity;
- suctioning fluid from the cavity through the passage of the grasper; and
- grasping the tissue to remove the tissue from the cavity.

80. The method of claim 79, further comprising the step of removing the cannula with the dilator remaining substantially in the expanded position.

81. The method of claim 79, wherein the leading end of the dilator includes a draw cable for drawing in the leading end, further comprising the step of pulling the draw cable to draw in the leading end of the dilator.

82. The method of claim 79, further comprising the step of removing the cannula with the dilator remaining substantially in the expanded position.

83. The method of claim 79, wherein the step of inserting the cannula includes inserting a cannula having a maximum diameter in the range of 3 mm to 5 mm.

84. The method of claim 79, wherein the step of suctioning includes the step of suctioning bite or other material from a gall bladder.

* * * * *

UNITED STATES PATENT AND TRADEMARK OFFICE
CERTIFICATE OF CORRECTION

PATENT NO.     : 6,958,069 B2
DATED          : October 25, 2005
INVENTOR(S)    : John I. Shipp et al.

It is certified that error appears in the above-identified patent and that said Letters Patent is hereby corrected as shown below:

Column 10,
Line 65, change "steps" to -- step --.

Column 11,
Line 60, change "to insert" to -- to be inserted --.

Column 12,
Line 21, change "moving" to -- removing --.

Column 13,
Lines 2 and 3, rewrite as follows:
-- animal or human body cavity, the extractor comprising:
    a body having a leading end, a trailing end, a longitudinal axis, --.
Line 42, after "dilator" add -- to move --.
Line 55, change "position" to -- position, --.
Line 57, change "a" to -- the --.

Column 14,
Line 5, delete "and".
Line 9, after "end" insert -- of --.
Line 14, delete "a".

Column 15,
Line 26, change "a" to -- at --.
Line 40, after "having" insert -- a --.
Line 41, change "expended" to -- expanded --.

UNITED STATES PATENT AND TRADEMARK OFFICE
CERTIFICATE OF CORRECTION

PATENT NO. : 6,958,069 B2
DATED : October 25, 2005
INVENTOR(S) : John I. Shipp et al.

It is certified that error appears in the above-identified patent and that said Letters Patent is hereby corrected as shown below:

Column 16,
Line 10, change "an" to -- and --.
Line 39, change "bite" to -- blle --.

Signed and Sealed this

Thirty-first Day of January, 2006

JON W. DUDAS
*Director of the United States Patent and Trademark Office*